Figure 1:
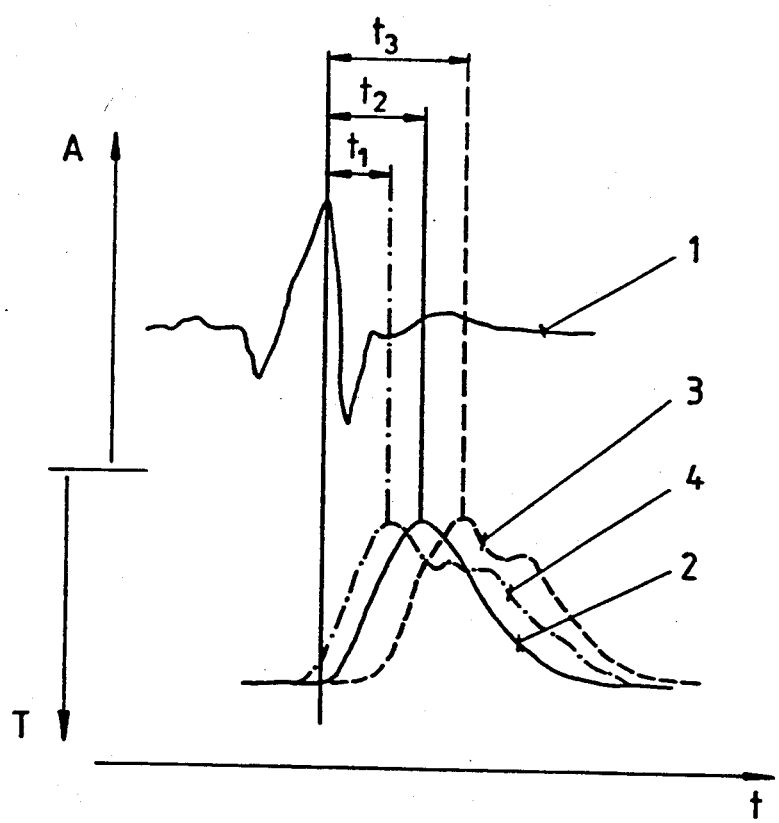

United States Patent [19]

Heinonen et al.

[11] Patent Number: 5,099,841

[45] Date of Patent: Mar. 31, 1992

[54] MEASUREMENT OF THE COMPOSITION OF BLOOD

[75] Inventors: Erkki O. Heinonen; Esa J. Tuulari, both of Helsinki; Mona Grönstrand, Lovisa, all of Finland

[73] Assignee: Instrumentarium Corporation, Finland

[21] Appl. No.: 478,258

[22] Filed: Feb. 5, 1990

[30] Foreign Application Priority Data

Feb. 6, 1989 [FI] Finland ................... 890552

[51] Int. Cl.$^5$ ............................... A61B 5/02
[52] U.S. Cl. ................... 128/633; 178/666; 178/670
[58] Field of Search ............... 128/633, 670, 690, 666, 128/687; 356/39, 40, 41

[56] References Cited

U.S. PATENT DOCUMENTS 4,224,948  9/1980  Cramer et al. ............... 128/690
4,928,642  5/1990  Goodman et al. ............... 128/633
4,934,372  6/1990  Corenmon et al. ............... 128/633

Primary Examiner—Kyle L. Howell
Assistant Examiner—Scott R. Akers
Attorney, Agent, or Firm—Andrus, Sceales, Starke & Sawall

[57] ABSTRACT

The invention relates to a method for synchronizing an optical arterial pulse signal (2, 3, 4), obtained by passing electromagnetic radiation through a tissue, with a detected signal (1) obtained from heartbeat. The delays of optical arterial pulses in relation to corresponding heartbeats are used to set up a time lapse, during the course of which there must appear an arterial pulse acceptable in the determination of blood composition. The position of time lapse in relation to detected heartbeat is repeatedly determined while continuing measurements from the obtained optical pulses occurring during the time lapse.

10 Claims, 1 Drawing Sheet

MEASUREMENT OF THE COMPOSITION OF BLOOD

The present invention relates to a method for synchronizing an optical arterial pulse signal, which has been obtained by allowing electromagnetic radiation to travel through a tissue, with a detected signal obtained from heartbeat.

The composition of blood can be measured noninvasively by means of lights of various colours. The pulsation of arterial blood causes a modulation in the light transmission signal used for measurement, the relative magnitude of said modulation on various wavelengths revealing the composition of blood.

The basic hypothesis for measurement is that the only originator of modulation is the arterial pulsation initiated by the mechanical function of the heart. However, modulation can also be caused by a movement, in which case an artifact may be introduced. In order to improve the reliability of measurement, the arterial pulses should be distinguished from artifacts as reliably as possible.

A generally used method in medical measurements is synchronization for improving the measurement information content. In most cases, synchronization utilizes the electrical heart function and the EKG-signal representative thereof and, preferably, its most distinguishable QRS-cycle. Such synchronizations include e.g. gamma imaging of the heart, wherein the EKG-cycle is divided into sequences and the imaging of successive EKG-cycles is integrated into these sequences, defibrillation wherein synchronization is used to prevent a defibrillation pulse from being simultaneous with a T-wave, cardiac pacemakers which detect electric activity of the heart and amplify it into a synchronizing pulse, ultrasound-operated kidneystone crushers wherein a crushing sound pulse is timed to be simultaneous with an arterial pulse for improving the conduction of ultrasonic energy as well as for distinguishing the arterial and artifact pulses in optical noninvasive measurements of the composition of blood.

The arterial blood pulsation signal obtained by noninvasively passing light around a tissue often includes faulty pulses which are caused by movements and attempts have been made to reduce their effect on measuring results by using the pulsation of arterial blood caused by the function of a patient's heart and detected from the modulation occurring in the light transmission signal, said pulsation being synchronized with the heartbeat which, in turn, is detected e.g. from an EKG-signal. This type of solution is disclosed e.g. in U.S. Pat. Nos. 4,802,486 and 4,928,612. The method described in involves measurement of the pulse frequency of an EKG-signal, the pulse frequency of the modulation of an optical signal, as well as the time lapse from a discovered EKG-pulse to a possible arterial pulse. When the pulse frequencies match with each other, the difference between the pulses is set as a time lapse during which the optical pulse must follow a pulse identified from the EKG-pulse in order to become acceptable as an arterial pulse and for the calculation of blood composition.

Since the time elapsed from the detection of an EKG-pulse to the detection of an arterial pulse is not always constant, there is recorded in memory the time lapse between the occurrence of e.g. the last four EKG-pulses and the associated arterial pulse in order to produce a time lapse or a so-called time window. After setting up a time window such time lapse remains constant. Only the optical pulses within such time window are taken into consideration. However, if the pulses are not detected within a certain period of time or during the course of predetermined number of pulses, the time elapsed from an EKG-pulse to the occurrence of an arterial pulse must be re-determined.

The method set forth in the above-cited patents involves problems in connection with measurements, since the delay of an optical pulse relative to an EKG-pulse varies a great deal depending, for example, on pulse frequency or nerve-related control. The fluctuation may be a result of e.g. treatments and algesias. Thus, the application of this method involves unnecessary pauses in the measurement of blood composition due to the fact that the position of a time window relative to an EKG-signal remains constant.

Timing the outset of a time window at the R-peak of EKG according to a known principle leads in most cases to poor specificity, since from the occurrence of the R-peak there is always some delay caused by mechanical heart action and propagation of a pressure wave before a mechanical arterial pulse can be measured. The pulses occurring during this delay are all artifacts. On the other hand, as the delay increases, the genuine arterial pulses no longer occur within the time window and become rejected, thus leading to a poorer sensitivity of selection.

An object of this invention is to eliminate the above problems. An object of the invention is to provide a reliable method which takes into consideration the delay of an optical pulse which varies relative to a detected heartbeat. Another object of the invention is to provide a detected heartbeat and optical signal synchronizing method which is at the same time both specific and sensitive.

The characterizing features of a method of the invention are set forth in the annexed claims.

The invention is based on the fact that the delay of an optical pulse relative to a detected heartbeat, such as e.g. an EKG-pulse, is an average of the time after which an optical pulse is likely to follow the EKG-pulse. This time average is set between the start and the finish of an allowed time period, preferably at the half-way point. The width of an allowed time period is preferably set to correspond to the deviation of detected delays.

Since the average delay is set at the half-way point through an allowed time period, the delay may vary in both directions without a genuine pulse becoming rejected, unlike in the prior known method in which the pulses exceeding the time lapse will be rejected. When the time period is increased or decreased according to delays measured form the optical pulses found within the time period, it is possible to achieve a continuous adjustment to the varying measuring situation.

The method can be used for essentially narrowing the allowed time period. With a typical pulse frequency of 70 beats/minute, a typical delay for an EKG-pulse and an optical pulse is 150 ms. In the prior known method, wherein the allowed time lapse begins at an EKG-pulse and ends at an optical pulse, the specificity ratio is 7.8. The specificity ratio refers to the proportion of an allowed time lapse to the duration of a pulse sequence. In a method of the invention, if the width of a time lapse is e.g. $\pm 2\% = 47$ ms, the ratio is 24 so the specificity is more than triple that of the prior art. The location of a varying time period serves also to improve sensitivity over the prior known method, since the method of the invention reacts to a changing measuring situation. In this invention, the delay of an optical pulse relative to an EKG-pulse is determined according to a generally known principle.

The invention will now be described in more detail with reference made to the accompanying drawing, in which FIG. 1 illustrates a varying time period set up by the application of a method of the invention from the delay between an EKG-signal and a separate, but simultaneously measured optical signal.

There are several devices available which are capable of measuring EKG-signals and transmission signals of lights of various colours required for carrying out this invention. One example of such is disclosed in the aforesaid U.S. Patents. Operation of the device is also described in the same patents. Since devices suitable for the purpose are prior known, the design and operation of such a device is not further explained.

FIG. 1 illustrates the amplitude (A) of an EKG-curve 1 representing the electric heart activity as a function of time. FIG. 1 illustrates also the information collected simultaneously from optical pulses 2, 3 and 4 as a function of transmittance (T) time (t). The optical pulse is obtained by allowing electromagnetic radiation to pass through a tissue, e.g. a finger.

As shown in FIG. 1, the optical pulse follows, by a slight delay the heartbeat detected in the EKG-curve. Furthermore, the occurrence of an optical pulse may fluctuate for various reasons even though the location of measurement remains the same is exactly what is described by curves 2, 3 and 4.

The initial moment of time measurement is preferably an R-wave identifiable from the EKG-signal. A time period $t_3 - t_1$ is developed considering the delay of optical pulses measured at various times. The time average for an optical pulse being likely to follow the R-wave of an EKG-signal is after a time $t_2$ and within time lapse $t_3 - t_1$.

Determination of the delay of an optical pulse is effected at the access stage by making sure that the pulse frequency measured from EKG and the frequency of an optical pulse remain unchanged. Thus, the delay will be accepted. The pulses occurring outside said time period $t_3 - t_1$ are artifacts and do not affect the time period.

The time period is preferably continuously revised by considering a variation in the delays of regularly measured optical pulses and by calculating the average duration of the delays. Thus, the position of the time period in relation to the R-wave of an EKG-signal changes as variations occur in the delays of optical signals. Thus, there will be no rejections of legitimate optical pulses but, instead, the continuously changing time period will be re-located according to the delays of optical signals.

A continuously changing time period makes it also possible to narrow the width of time period $t_3 - t_1$. Thus, a narrow time lapse can be accepted without a risk of rejecting the optical pulse since a variation in the delay of an optical pulse in relation to the EKG-signal is continuously taken into consideration This is why both sensitivity and specificity improve.

The invention is by no means limited to the above embodiments but various details of the invention can be revised within the scope of the claims In the embodiment described in connection with the drawing, the time period had a width which remained unchanged throughout the measurement. It is self-evident that the time period can also be narrowed or widened during the measurement if this is called for by the delay of measured optical pulses.

It is common knowledge that heartbeat can be detected not only from an EKG-curve but by other methods as well. What is important is to obtain two mutually independent signals from a past heartbeat.

What is claimed is:

1. A method for synchronizing an arterial signal with a heartbeat signal so that blood composition can be accurately determined by analysis of the arterial signal, said arterial signal being obtained by passing electromagnetic radiation through tissue at location removed from that of the heart and being pulse-like in nature as a result of the pulsatile movement of blood through the tissue by the heartbeat of the heart, said method comprising the steps of:

detecting the occurrence of an identifiable aspect of a heartbeat signal;

ascertaining a point in time at which a pulse occurs in the arterial signal following the occurrence of an identifiable aspect of a given heartbeat signal;

establishing a time period which includes said pulse in the arterial signal, said time period commencing after an interval following the occurrence of the identifiable aspect of the heartbeat, the commencement and conclusion of the period of time respectively preceding and succeeding the point in time by predetermined amounts;

accepting arterial signals appearing within said time period for analysis to determine blood composition;

repeating the ascertainment of the point in time for heartbeat signals occurring subsequent to the given heartbeat signal; and re-establishing the time period with respect to the heartbeat signal as a result of said subsequent ascertainment.

2. The method according to claim 1 further defined as repeating the ascertainment of the point in time for each arterial signal having a pulse appearing within said time period.

3. The method according to claim 1 further defined as averaging the occurrences of the pulses in the arterial signals for a plurality of heartbeats in ascertaining the point in time.

4. The method according to claim 1 further defined as maintaining the duration of the time period constant.

5. The method according to claim 1 further defined as altering the duration of the time period.

6. The method according to claim 1 further defined as altering the predetermined amount of time by which the commencement or conclusion of the time period precedes or succeeds the point in time.

7. The method according to claim 4 further defined as altering the predetermined amount of time by which the commencement or conclusion of the time period precedes or succeeds the point in time.

8. The method according to claim 5 further defined as altering the predetermined amount of time by which the commencement or conclusion of the time period precedes or succeeds the point in time.

9. The method according to claim 1 further defined as determining the occurrence of an identifiable aspect of the heartbeat signal by detecting an EKG signal of the heart.

10. The method according to claim 1 further defined as one for determining blood composition and as including the step of analyzing arterial signals occurring within the time period to determine blood composition.

* * * * *